United States Patent [19]  
Leang et al.

[11] Patent Number: 4,913,162  
[45] Date of Patent: Apr. 3, 1990

[54] NOCTURNAL PENILE TUMESCENE AND RIGIDITY MONITOR

[75] Inventors: William N. Leang; Larry J. Brick, both of Caledonia, Wis.

[73] Assignee: Medical Engineering Corporation, Racine, Wis.

[21] Appl. No.: 200,040

[22] Filed: May 27, 1988

[51] Int. Cl.⁴ .............................................. A61B 5/10
[52] U.S. Cl. ...................................... 128/774; 33/512
[58] Field of Search ....................... 128/774, 782, 694; 33/511, 512

[56] References Cited

U.S. PATENT DOCUMENTS

| 4,469,108 | 9/1984 | Goldstein | 128/774 |
| 4,474,187 | 10/1984 | Timm et al. | 128/694 |
| 4,515,166 | 5/1985 | Timm | 128/694 |
| 4,606,353 | 8/1986 | Timm | 128/774 |
| 4,766,909 | 8/1988 | Timm et al. | 128/774 |

Primary Examiner—Kyle L. Howell  
Assistant Examiner—John C. Hanley  
Attorney, Agent, or Firm—Rodman & Rodman

[57] ABSTRACT

The nocturnal penile tumescene and rigidity sensor device includes a flexible, foldable member that supports a relatively soft foam material and a relatively hard foam material. In one embodiment of the invention the relatively soft foam material and the relatively hard foam material cooperate with corresponding force-sensing resistors to detect changes in penile tumescence and rigidity. The relatively soft foam material detects changes in penile tumescence whereas the relatively hard foam material and its corresponding force-sensing resistor detect the presence and/or changes in penile rigidity. In another embodiment of the invention, a relatively soft foam material and a relatively hard foam material, formed of conductive foams, are shaped to contact a conductive strip with preselected different areas of surface contact in response to different levels of tumescence and rigidity. The change of contact area between the conductive foams and the conductive strip is detected and recorded. In either embodiment of the invention the sensor device can be trimmed to conform exactly to the penile contour of a patient, and when testing is completed the sensor device is disposable.

27 Claims, 8 Drawing Sheets

HARD FOAM
RIGID

HARD FOAM
NOT RIGID

SOFT FOAM
RIGID

SOFT FOAM
NOT RIGID

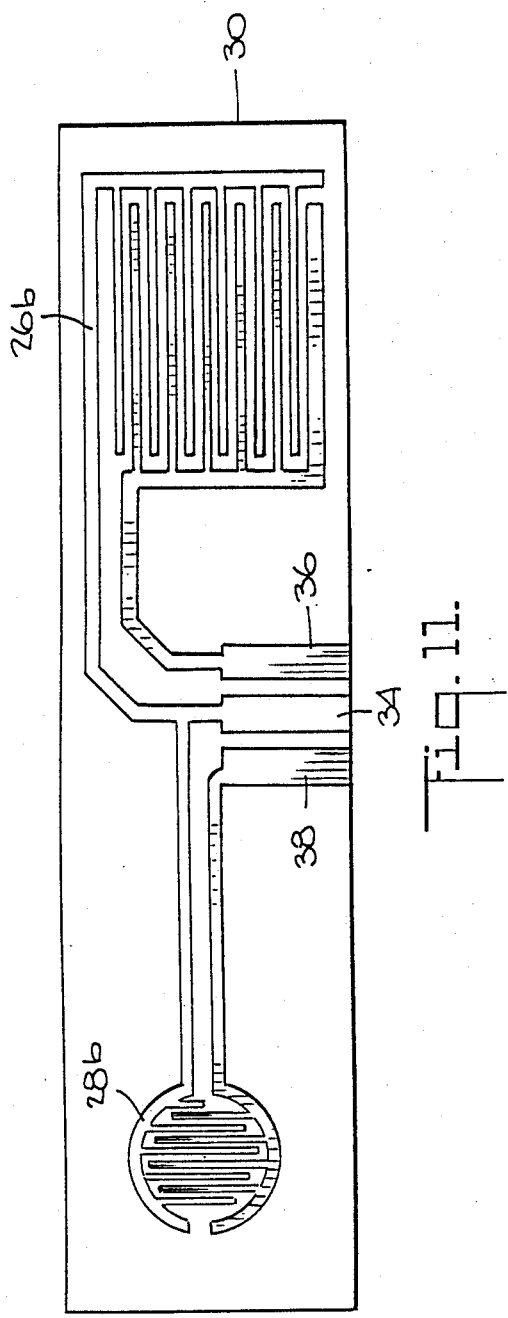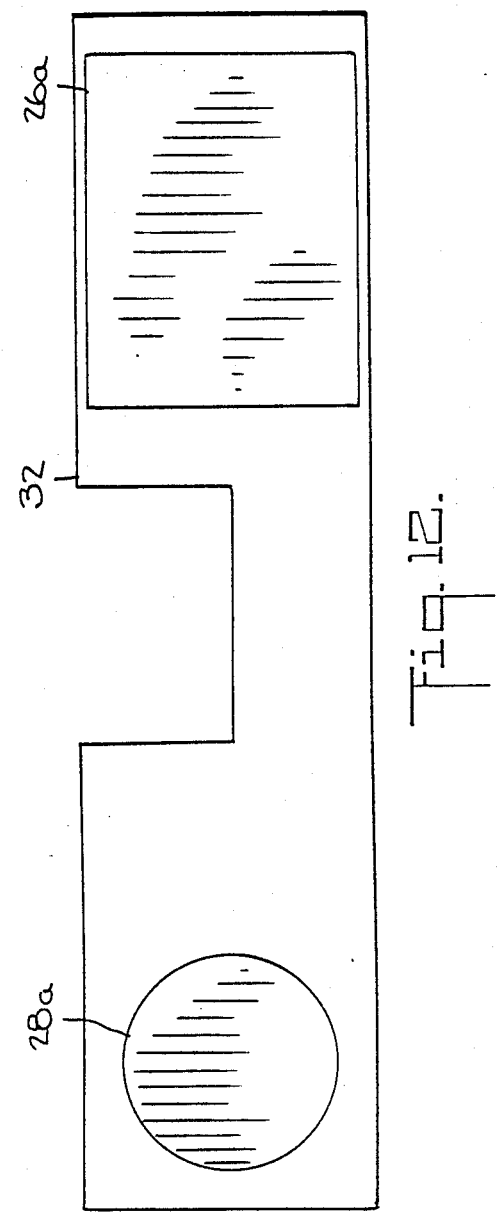

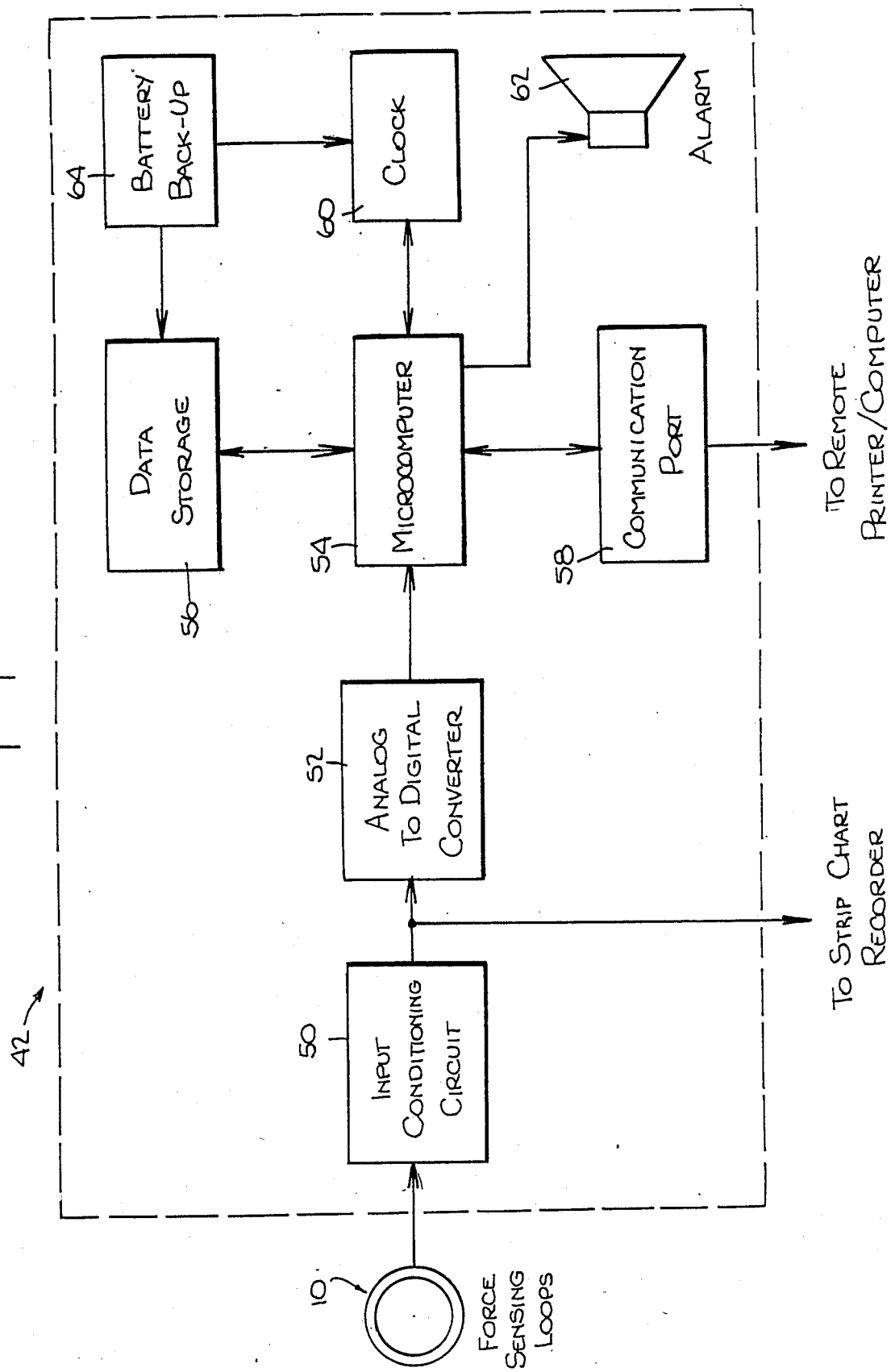

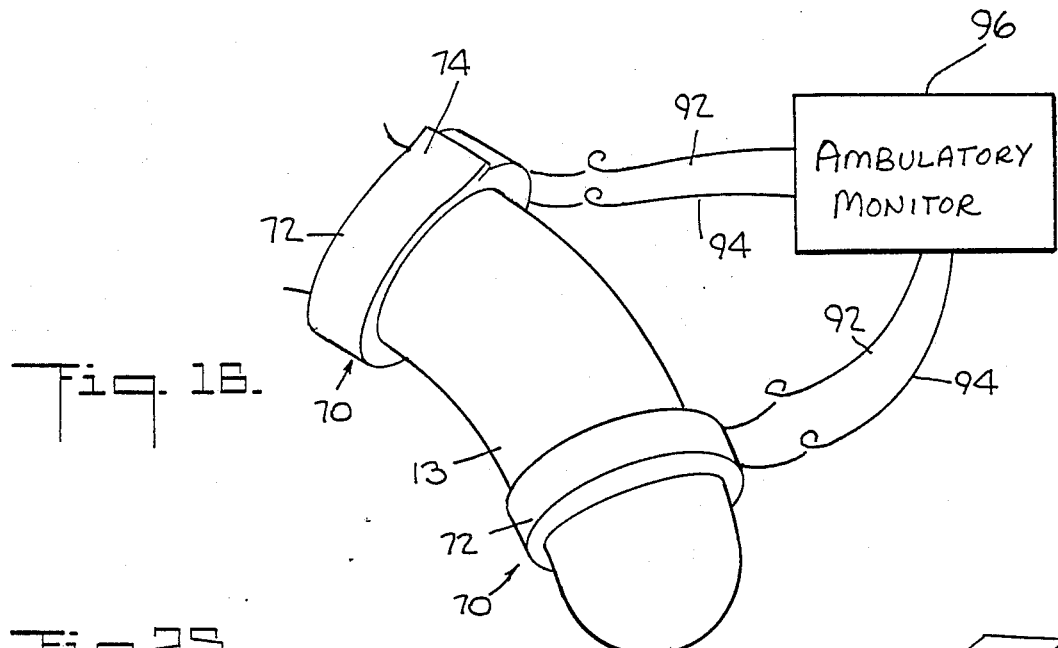
Fig. 1B.
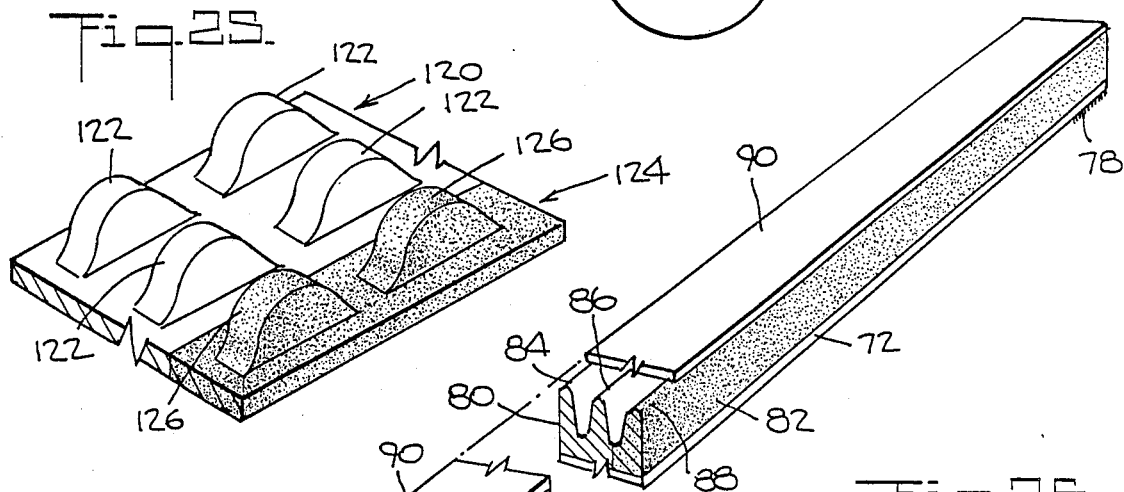
Fig. 25.
Fig. 17.
Fig. 26.
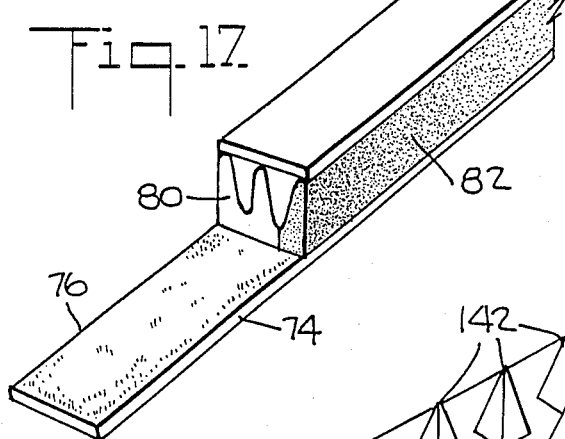
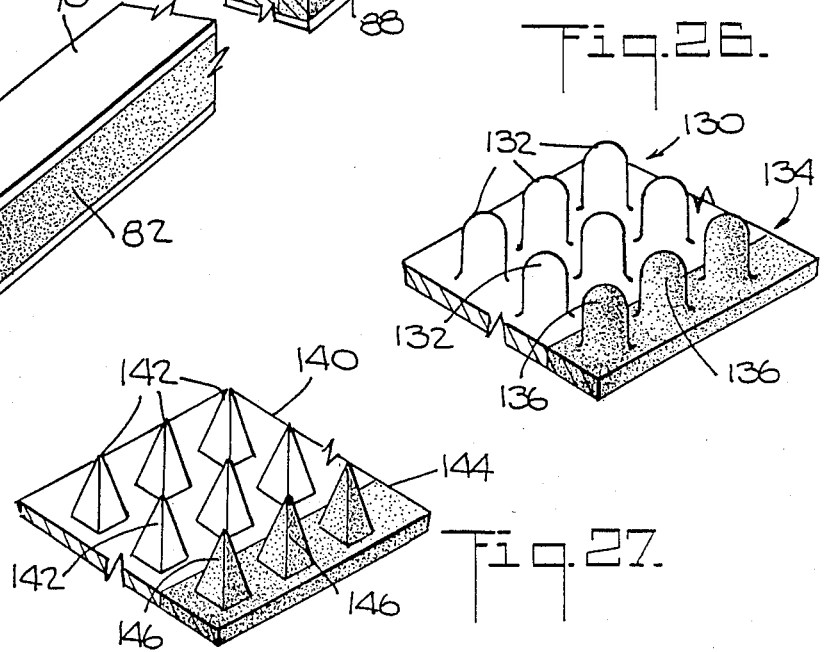
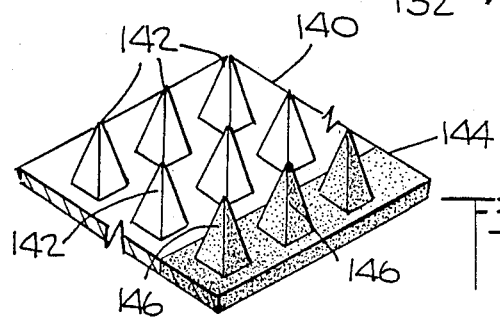
Fig. 27.

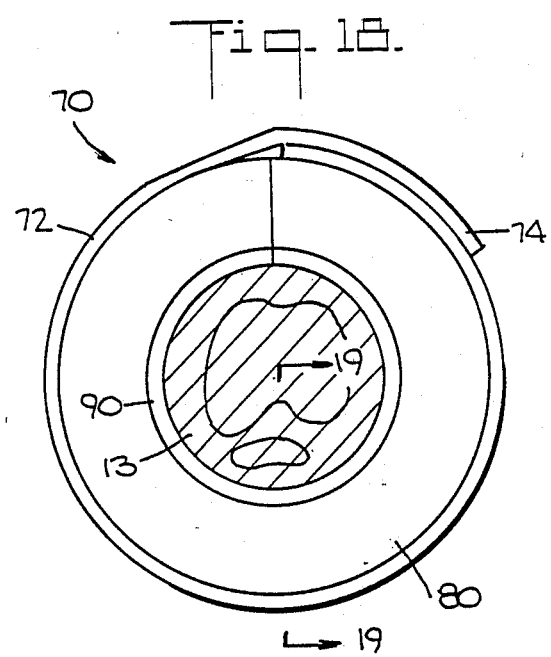
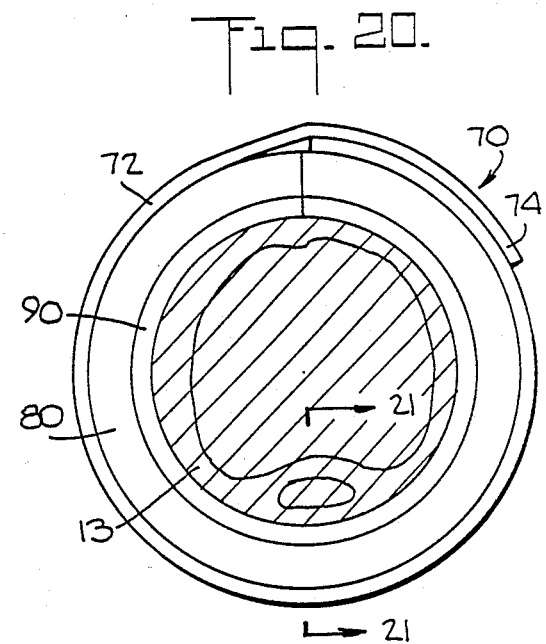
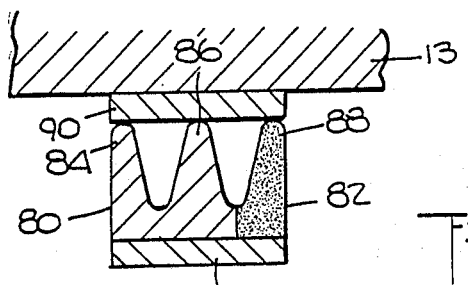
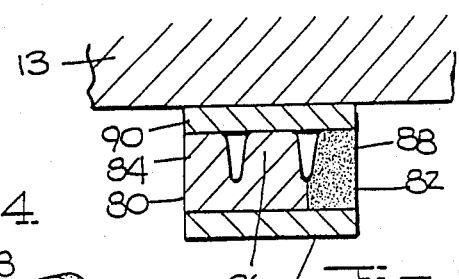
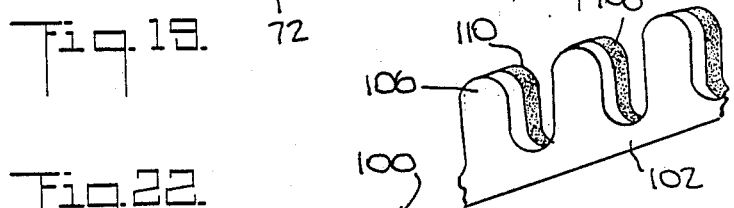
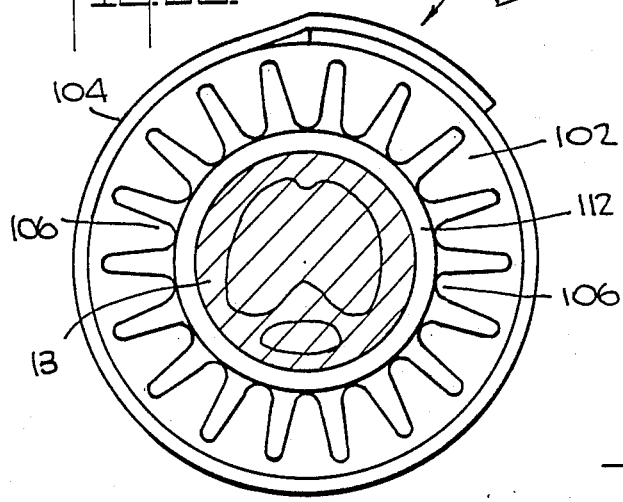
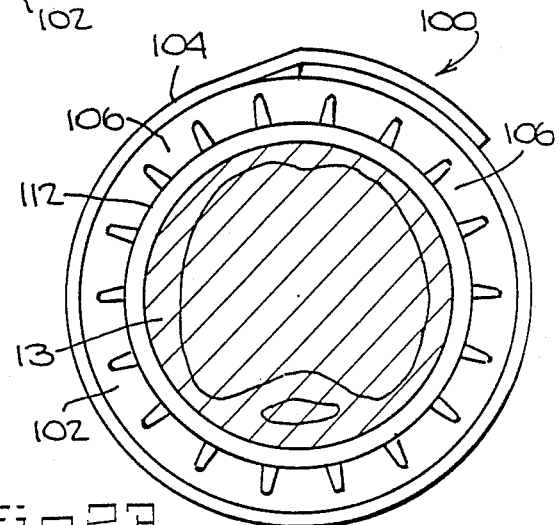

NOCTURNAL PENILE TUMESCENE AND RIGIDITY MONITOR

BACKGROUND OF THE INVENTION

This invention is directed to nocturnal penile tumescence and rigidity monitoring devices and more particularly to a novel flexible, adjustable, disposable, sensing device and method for monitoring penile tumescence and rigidity.

Nocturnal penile tumescence monitoring has become widely used as a diagnostic procedure for determining whether male impotency is psychogenic or organic. A known device for monitoring penile tumescence, as shown in PCT Publication No. W083/03748, includes strain gauges placed in two penile locations to measure increases and decreases in penile tumescence during nocturnal periods.

A recent article entitled "Development of a Penile Rigidity Indicator and New Concepts in the Quantification of Rigidity" by K. M. Desai et al. in the 1988 British Journal of Urology, pp. 254–60, states that the measurement of girth change alone "is prone to diagnostic misinterpretation since increase in penile circumference is not synonomous with rigidity and significant expansion may occur in the absence of a rigid erection."

Thus the monitoring of penile rigidity as well as tumescence is believed helpful in diagnosing male impotency, since penile tumescence without the requisite rigidity will usually not suffice to effect vaginal penetration.

The aforementioned British Journal of Urology article describes a PERIN device (Penile Rigidity Indicator) capable of monitoring rigidity as well as tumescence, citing an apparently unpublished Great Britain Patent No. 82708215. The PERIN device for measuring penile rigidity and tumescence, as disclosed in the foregoing article, includes a sensor that is retained around the penis using a foam strap fastened with Velcro tape. The foam strap maintains a retaining force at a relatively constant level during various phases of erection.

The PERIN sensor consists of a contoured platform with a protruding stylus. The stylus is mounted on a pivoted lever which acts on a spring beam having resistance strain gauges that indicate an applied force. The sensor includes tongs made of pliable plastic material which incorporate a metal strain gauge for simultaneous girth monitoring. The sensor stylus makes direct contact with the tunica albuginea of the penis.

The pliable plastic tongs permit fitting of the sensor onto different subjects and the device is thus reusable, with the sensor being permanently wired to a data conversion device.

Consequently there is a need to sanitize the PERIN device each time it is used. In addition, the pliable plastic tongs of the PERIN device are not easily adaptable to exactly conform to a penile contour. Thus the PERIN monitoring system may be subject to calibration errors.

Another known device for measuring penile tumescence and rigidity is disclosed in U.S. Pat. 4,515,166. The disclosed device employs a cable that forms a noose-like fitting around the penis, and a sprocket arrangement that may also be subject to calibration errors. The disclosed system for measuring penile rigidity includes a torque motor on an elongated member that encircles the penis. The use of cable displacement as a measure of compressibility or rigidity is a relatively cumbersome arrangement that can be discomforting to the user.

It is thus desirable to provide a sensing device for monitoring penile tumescence and rigidity which can be easily installed on a patent, conforms exactly to a penile contour, is comfortable to use during nocturnal periods, and is disposable after use.

OBJECTS AND SUMMARY OF THE INVENTION

Among the several objects of the invention may be noted the provision of a novel nocturnal penile tumescence and rigidity sensing device, a novel nocturnal penile tumescence and rigidity sensing device which is foldable and flexible for easy installation, a novel nocturnal penile tumescence and rigidity sensing device that can be trimmed to a desired size to conform exactly to a penile contour, a novel nocturnal penile tumescence and rigidity sensing device that can be easily and accurately calibrated, a novel nocturnal penile tumescence and rigidity sensing device that is disposable, a novel nocturnal penile tumescence and rigidity sensing device with tumescence and rigidity sensors on a flexible, foldable member, a novel nocturnal penile tumescence and rigidity sensing device which utilizes two different types of foam material for sensing respective changes in tumescence and rigidity, a novel nocturnal penile tumescence and rigidity sensing device that includes two different types of conductive foam material for transmitting tumescence and rigidity sensor signals, a novel nocturnal penile tumescence and rigidity sensing device which incorporates two different types of foam material for transmitting respective forces associated with tumescence and rigidity to corresponding signal producing agents, a novel nocturnal penile tumescence and rigidity monitor that can be looped around the penis to provide data relating to penile tumescence and rigidity, and a novel method of measuring penile tumescence and rigidity.

Other objects and features of the invention will be in part apparent and in part pointed out hereinafter.

The nocturnal penile tumescence and rigidity sensor, in accordance with the present invention, includes a flexible, foldable, member having tumescence and rigidity sensing means. The flexible, foldable, member can be looped around a penis and detachably secured in the loop arrangement to conform exactly to the penile contour.

In one embodiment of the invention, the tumescence sensing means include a first relatively soft compressible foam material and a first force-sensing resistor joined to the flexible, foldable member. The first force-sensing resistor is sandwiched between the first foam material and the foldable member. The rigidity sensing means includes a second relatively noncompressible foam material, and a second force-sensing resistor joined to the flexible, foldable member. The second force-sensing resistor is sandwiched between the second foam material and the foldable member.

When tumescence and rigidity monitoring is to begin the sensor device is looped around the penis and connected to a signal conversion or monitoring device which feeds current to the force-sensing resistors of the sensor device. A base line calibration is made of voltage signals from the sensor device that correspond to preselected dimensional characteristics of the penis in a flaccid, non-rigid condition.

As penile tumescence develops the penis will compress the relatively soft foam material to exert a force on the first force-sensing resistor. Changes in a voltage signal from the first force-sensing resistor corresponding to changes in force or compression on the relatively soft foam material will indicate the various levels of tumescence that develop during the monitoring procedure.

The relatively noncompressible foam material is selected to resist compression by the penis, even when the penis is in a rigid state. Consequently, penile tumescence in the absence of rigidity will be insufficient to transmit any significant force variations through the second foam material to the second force sensing resistor. Thus penile tumescence without rigidity will have little or no effect on the second force-sensing resistor associated with the second foam material. When the penis develops rigidity, a penile force is exerted on the second foam material to cause a change in the characteristics of the second force-sensing resistor. The second force-sensing resistor associated with the second foam material will emit a change of signal corresponding to the level of rigidity.

The signals provided by the force-sensing resistors can be used to provide data for a continuous plot of penile tumescence and rigidity or can be stored for later transcription by a remote printer or computer.

In another embodiment of the invention, the tumescence sensing means includes a relatively soft conductive foam material supported on a flexible foldable member and the rigidity sensing means includes a relatively hard conductive foam material also supported on the flexible foldable member. The foam materials are shaped to provide crests or corrugations that contact a conductive strip with a preselected contact area. An initial contact area corresponding to a flaccid, nonrigid condition of the penis is used as a base line when testing begins. During testing, when tumescence increases, the contact area between the relatively soft conductive foam material and the conductive strip increases. If rigidity is not present, the area of contact between the relatively hard conductive foam material and the conductive strip does not change. As rigidity develops the contact area between the relatively hard foam material and the conductive strip also increases.

As the area of contact between the conductive foam materials and the conductive strip increases, a change of signal corresponding to the increased contact area is emitted from the sensor device. The change of signal is correlatable with penile tumescence and rigidity, and such signal data is fed into a monitoring device which provides a graphic readout of tumescence and rigidity and/or stores such data for later retrieval.

In either embodiment of the invention the sensor device can be trimmed to a desired size and disposed of when testing is completed.

The invention accordingly comprises the constructions and method hereinafter described, the scope of the invention being indicated in the claims.

DESCRIPTION OF THE DRAWINGS

In the accompanying drawings,

FIG. 11 is an enlarged fragmentary plan view of the grid strips of the sensing device;

FIG. 12 is a plan view of force-sensing resistor strips of the sensing device;

FIG. 13 is a simplified schematic block diagram of a monitoring device for the nocturnal penile tumescence and rigidity sensing device;

FIG. 16 is a simplified perspective view of a pair of nocturnal penile tumescence and rigidity sensor devices, in a monitoring position, incorporating another embodiment of the invention;

FIG. 17 is a simplified perspective view of an unlooped sensing device prior to placement in a monitoring position;

FIG. 18 is an enlarged front view thereof, partly shown in section, after placement in the monitoring position on a flaccid penis;

FIG. 19 is a sectional view taken on the line 19—19 of FIG. 18;

FIG. 20 is a view similar to FIG. 18 with the penis in a tumescent condition;

FIG. 21 is a sectional view thereof taken on the line 21—21 of FIG. 20;

FIG. 22 is a front view, partly shown in section, of a further embodiment of the invention after placement in a monitoring position on a flaccid penis;

FIG. 23 is a view similar to FIG. 22 with the penis in a tumescent condition;

FIG. 24 is a fragmentary perspective detail thereof; and

FIGS. 25-27 are simplified perspective views of conductive foam materials used in other embodiments of the invention.

Corresponding reference characters indicate corresponding parts throughout the several views of the drawings.

DETAILED DESCRIPTION OF THE INVENTION

Figure 1:
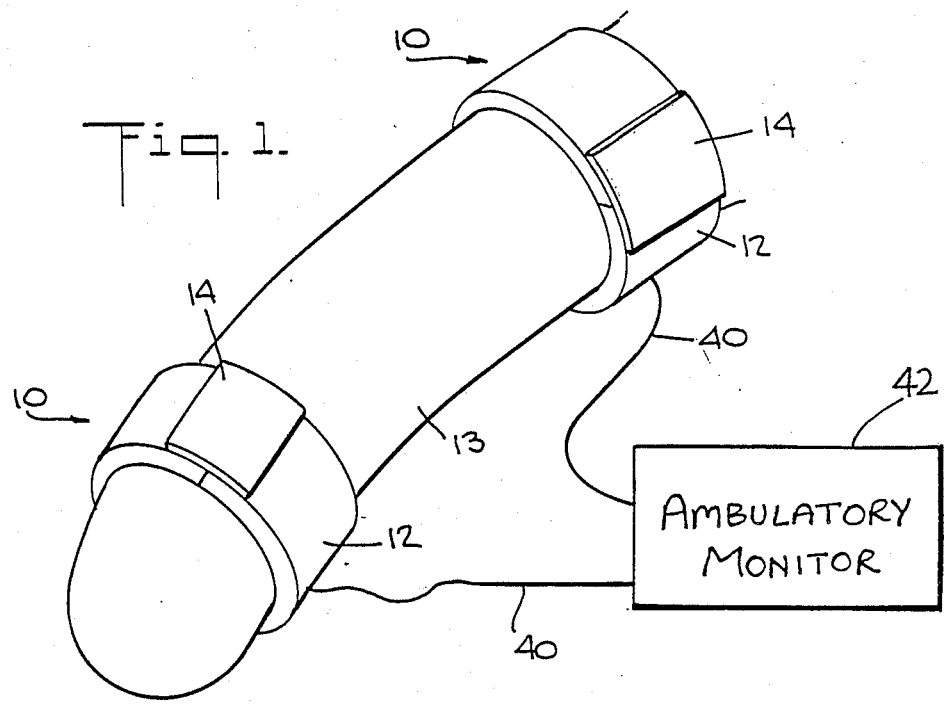
FIG. 1 is a simplified perspective view of a pair of nocturnal penile tumescence and rigidity sensing devices, in a monitoring position, incorporating one embodiment of the invention.

A tumescence and rigidity sensor for a nocturnal penile tumescence and rigidity monitor incorporating one embodiment of the invention is generally indicated by the reference number 10 in FIG. 1.

The tumescence and rigidity sensor 10 includes a flexible, foldable member 12 made of a suitable fabric material such as dacron. The foldable member 12 is of sufficient length to encircle a penis 13 in a flaccid condition. A securement member 14, which can also be formed of dacron, is provided at one end of the foldable member 12, extending beyond the end portion.

Figure 2:
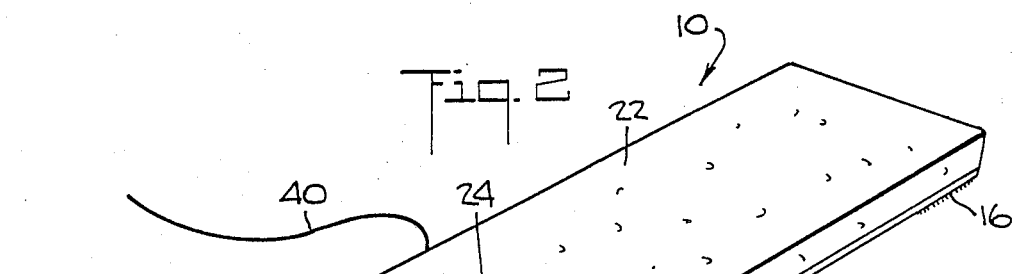
FIG. 2 is a simplified perspective view of an unlooped sensing device prior to placement in the monitoring position.
Figure 4:
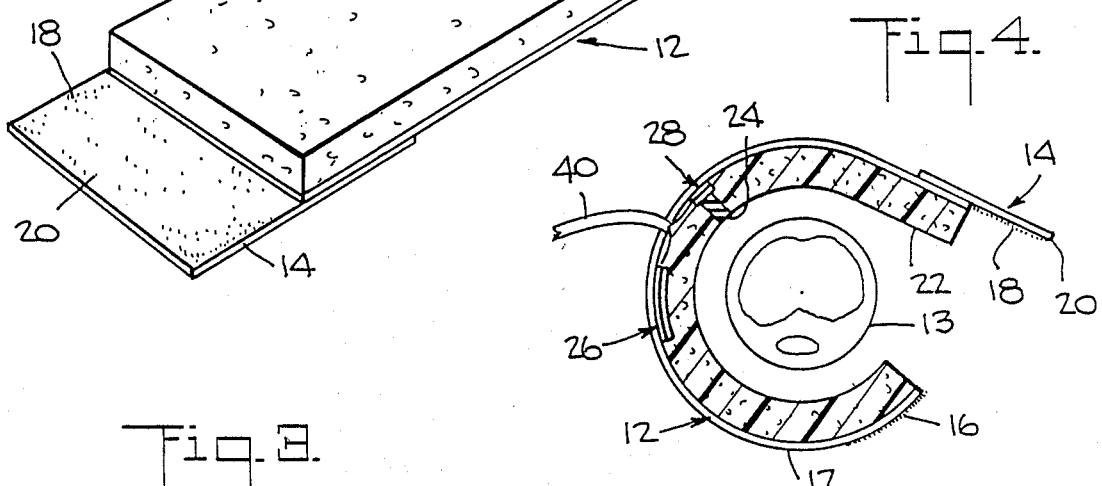
FIG. 4 is a sectional view of a partially looped sensing device prior to placement in the monitoring position.
Figure 3:
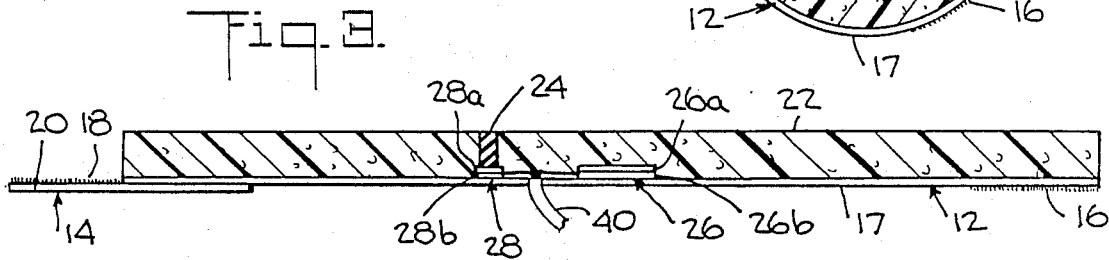
FIG. 3 is a sectional view thereof.

Referring to FIGS. 2-4, attachment means such as soft Velcro ® mesh 16 is provided on a surface 17 of the flexible, foldable member 12, and can cover the full extent of the surface 17. Velcro ® hooks 18 are provided on a surface 20 of the securement member 14 and can cover the full extent of the surface 20. Under this arrangement a portion of the securement member 14 is detachably secured to the foldable member 12 by engagement of the Velcro mesh 16 with the Velcro hooks 18. The remaining portion of the securement member 14 that extends from the foldable member 12 is attachable to the opposite end of the foldable member 12 to hold the foldable member in a looped configuration as shown for example, in FIG. 1.

A relatively soft compressible foam material 22, which can be formed of Polyether, for example, such as made by Scot Foam of Chester, Pennsylvania, is joined to the flexible, foldable member 12 and preferably extends the full length and width of such foldable member 12.

A relatively hard foam material 24 in the form of a cylindrical plug is provided on the foldable member 12 within the array of the soft foam material 22. The foam material 24 can be formed of closed cell neoprene such as made by Minor Rubber Co. of Bloomfield, New Jersey.

A pair of force-sensing resistors 26 and 28 are respectively provided between the foldable member 12 and the foam materials 22 and 24. The force sensing resistors 26 and 28 can be of the type manufactured by Interlink Electronics of Santa Barbara, Calif., as announced at page 58 of Machine Design Magazine, Jan. 8, 1987, and disclosed in one or more of the following patents: 4,451,714; 4,276,538; 4,314,228; and 4,301,337.

As most clearly shown in FIG. 3, the force-sensing resistor 26 comprises a laminate of a generally rectangular resistor strip 26a and a generally rectangular grid strip 26b. The force-sensing resistor 28 comprises a laminate of a generally circular resistor strip 28a and a generally circular grid strip 28b, both of which are of a size that approximately corresponds to the cross-sectional size of the foam material 24.

The force-sensing resistors 26 and 28 are sufficiently spaced to assure separate and distinct compilations of data for each resistor. Preferably the force-sensing resistor strips 26a and 28a are supported on a single substrate material such as a Mylar or Ultem backing 30, shown dotted in FIG. 11. In addition, the grid strips 26b and 28b can be supported on a single Mylar or Ultem backing 32, shown dotted in FIG. 12.

Referring to FIG. 11, the grid strips 26b and 28b include a common ground terminal 34. A terminal 36 extends from the grid portion 26b and a terminal 38 extends from the grid portion 28b. A cable member 40 (FIG. 3) extends from the terminals 34, 36 and 38 in any suitable known manner and detachably connects to an ambulatory monitoring unit 42.

The ambulatory monitor 42 includes a power supply battery (not shown) that supplies a current to the force-sensing resistors 26 and 28 of the sensor device 10. The power supply battery can be a single 9-volt DC battery that may be replaced or recharged.

Referring to FIG. 13, the monitor 42 also includes an input conditioning circuit 50, an analog-to-digital converter 52, a microcomputer 54, a data storage unit 56, a communication port 58, a clock 60, an alarm 62 and a back-up battery 64. The ambulatory monitor 42 is made sufficiently small to be comfortably secured to a patient, and if desired can be worn around a patient's waist or thigh during monitoring.

In using the sensor device 10, the flexible, foldable member 12 is formed into a loop around the penis 13 when the penis is in the flaccid state. The securement member 14, at one end of the foldable member 12, is joined to the other end of the flexible member 12 in the manner indicated in FIG. 4. The flexible, foldable member 12, including the foam material 22 and the Velcro mesh 16 can be trimmed with scissors, for example, to enable the sensor device 10 to exactly conform to the circumference of the penis 13.

As noted in FIG. 4, the inner layer of the sensor device 10, when formed into a loop comprises the soft compressible foam material 22 and the relatively hard foam material 24, both of which come into direct contact with the penis 13.

Figure 5:
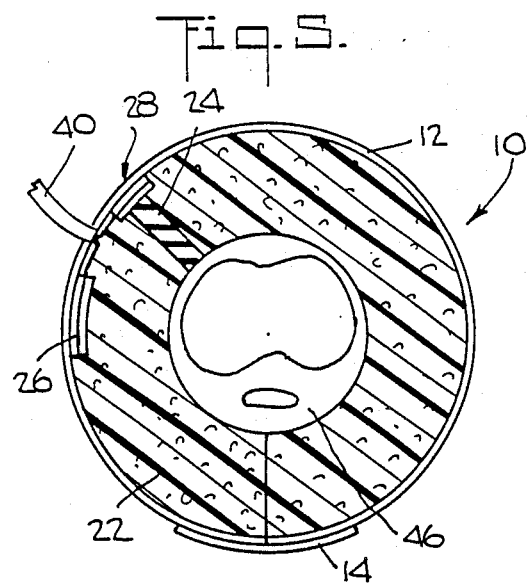
FIG. 5 is an enlarged sectional view thereof after placement in the monitoring position on a flaccid penis.
Figure 6:
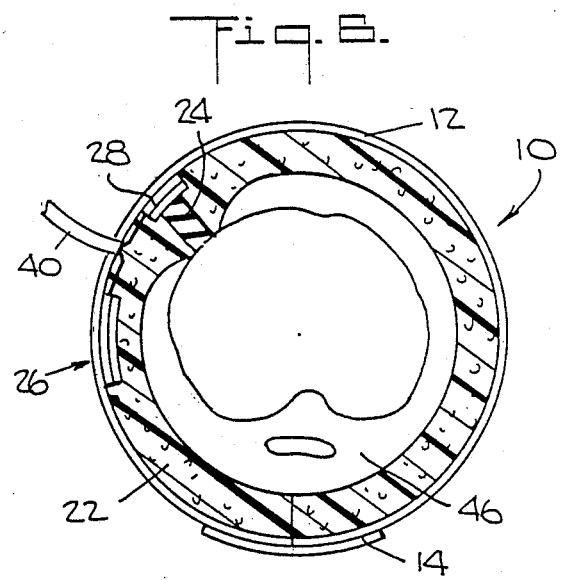
FIG. 6 is a view similar to FIG. 5 with the penis in a tumescent condition.

When the sensor device 10 is looped around the penis 13, it is desirable to align the force-sensing resistors 26 and 28 away from the urethra 46 such as, for example, by orienting the sensor 10 on the penis 13 in the manner shown in FIGS. 5 and 6.

As shown in FIG. 1, one sensor device 10 can be located at the base of the penis 13 and another sensor device 10 can be located at the tip portion of the penis 13. If desired, the cable 40 for each of the sensor devices 10 can be color coded to indicate proper connection to the monitoring unit 42. Although not shown, each of the cables 40 include known detachable connectors for detachable securement to the monitoring unit 42.

The monitoring process is carried out when the sensor devices 10 are positioned at the base and tip portions of the penis 13 and the cables 40 are connected to the ambulatory monitor 42. Under this arrangement, the force-sensing resistors 26 and 28 of each sensor device 10 transmit a voltage signal to the monitor 42 that changes in accordance with conditions of tumescence and rigidity present in the patient being monitored.

For example, when the penis 13 is in a flaccid condition and relatively little pressure is exerted on the force-sensing resistors 26 and 28, there is normally low surface-to-surface contact between the respective force-sensing resistor strips 26a, 28a and the corresponding grid strips 26b, 28b. The force-sensing resistors 26 and 28 thus have a normally high resistance level and furnish correspondingly high voltage signals to the monitor 42.

When penile tumescence increases, as shown in FIG. 6, the penis 13 compresses the relatively soft foam material 22 thereby exerting a force on the force-sensing resistor 26. The magnitude of force exerted on the force-sensing resistor 26 is proportional to the level of tumescence developed in the penis. The force imposed by the penis 13 on the force-sensing resistor 26 through the soft foam material 22 lowers the resistance of the force-sensing resistor 26. The force-sensing resistor 26 thus transmits a relatively low voltage signal in comparison with the voltage signal that corresponds to a flaccid penis.

If penile tumescence is not accompanied by penile rigidity, the penis 13 will be unable to exert a force on the relatively hard foam material 24. Consequently there will be little or no change in resistance of the force-sensing resistor 28.

The relatively hard foam 24 is selected to resist compression by the penis and acts in a fashion similar to a hardness tester such as a Durometer. The resistance to compression (or penetration) is detected by the force-sensing resistor 28 which sends a signal to the ambulatory monitor 42 that is used in calculating the degree of rigidity. Under this arrangement the force-sensing resistor 28 will continue to transmit a relatively high voltage signal corresponding to an absence of rigidity, even though the penis may be in a tumescent condition.

When penile rigidity is present, the penis 13 exerts a force on the relatively hard foam material 24 causing the resistance of the force-sensing resistor 28 to lower and transmit a relatively low voltage signal to the ambulatory monitor 42.

Since conditions at the base and tip of the penis 13 can vary, it is beneficial to provide data for both locations.

Low level voltage signals can be correlated with a high sensor output to provide the graphs of FIGS. 7–10 which indicate that increases in penile tumescence are not necessarily accompanied by the presence of penile rigidity.

Figure 7:
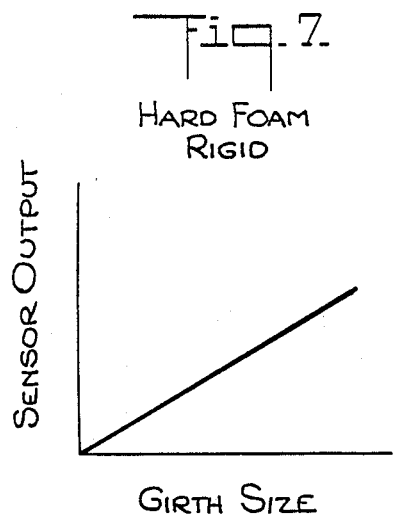
FIGS. 7-10 are graphs of sensor output versus girth size for the two different types of foam used in the sensing device.
Figure 8:
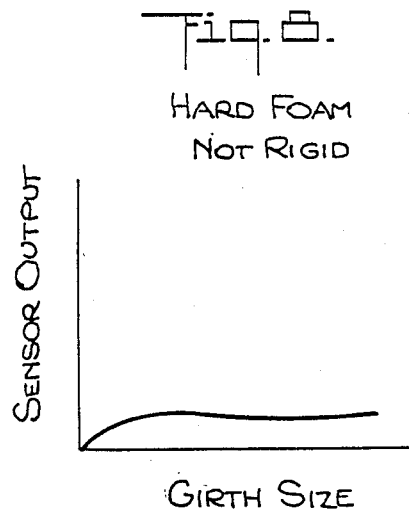
Figure 9:
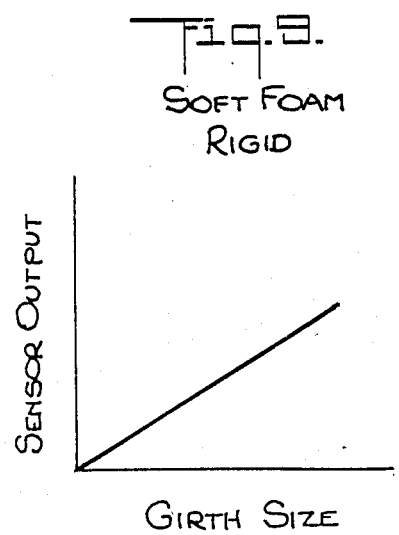
Figure 10:
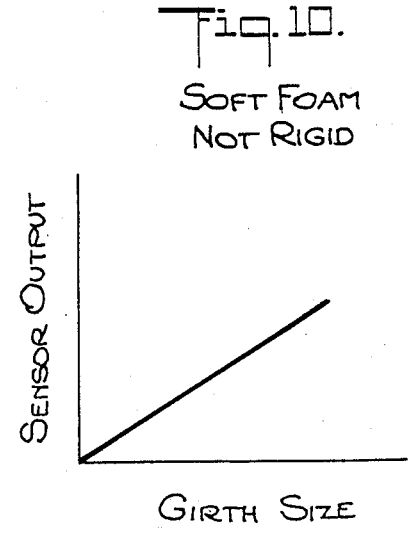

FIGS. 7 and 8 also confirm that penile rigidity is usually present only during increases in penile tumescence, and that penile rigidity can be absent even when penile tumescence is present.

During monitoring, the voltage signals from the sensor device 10 are fed into the ambulatory monitor 42 for conditioning by the input conditioning circuit 50 which amplifies the voltage signals. The amplified voltage signals are fed into the analog-to-digital converter 52 and can also be fed to a strip chart recorder (not shown).

The strip chart recorder makes a real time analog plot of the voltage that goes into the input conditioning circuit 50 during a monitoring session. The analog plots indicate changes in penile circumference as a measure of penile tumescence and buckling force as a measure of penile rigidity.

The analog-to-digital converter 52 converts the amplified signal to a digital format for processing by the microcomputer 54. The signal that is processed by the microcomputer is stored in a data storage unit 56 and can also be converted to software that is fed into the communication port 58 that leads to a remote printer or computer (not shown).

The clock 60 is a measure of the real time for the data being stored in the data storage unit 56. The battery backup 64, which can be a 3-volt lithium battery, powers the clock 60 and the data storage unit 56 enabling the data storage unit to retain data in the storage memory and in the real time clock.

The alarm 62, included in the monitor 42, can be optionally set to sound in response to a preselected amplitude signal from the sensor 10 that corresponds to a preselected level of tumescence and/or rigidity. The alarm 62 serves to arouse a patient to enable the patient to recognize that his impotence is psychological and not organic.

Figure 15:
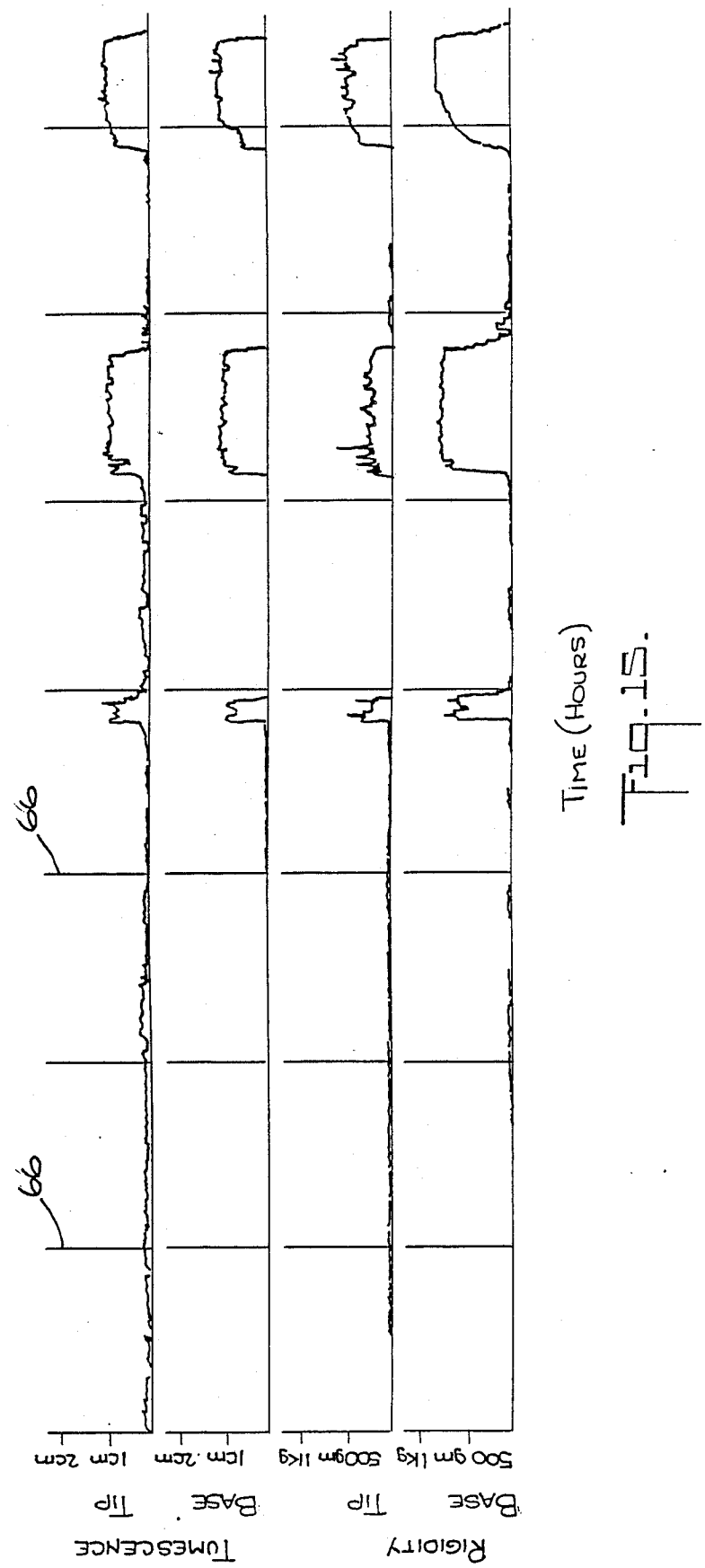
FIG. 15 shows simplified schematic plots of tumescence and rigidity.

When testing is completed, the monitor can be brought to a clinician and connected to a recorder/printer to print the stored tumescence and rigidity data in a format such as shown in FIG. 15, wherein tumescence and rigidity changes are plotted on an hourly basis.

Referring to FIG. 15, tumescence changes can be expressed in centimeters, and, for example, can range from 0 to 4 cm., plus or minus 20%. Rigidity can be expressed in grams of buckling force and can range, for example, from 0 to 1000 grams, plus or minus 20%. Hourly increments are indicated by the lines 66. The recorded data in the monitor 42 can also be downloaded to a personal computer for further processing and analysis.

Figure 14:
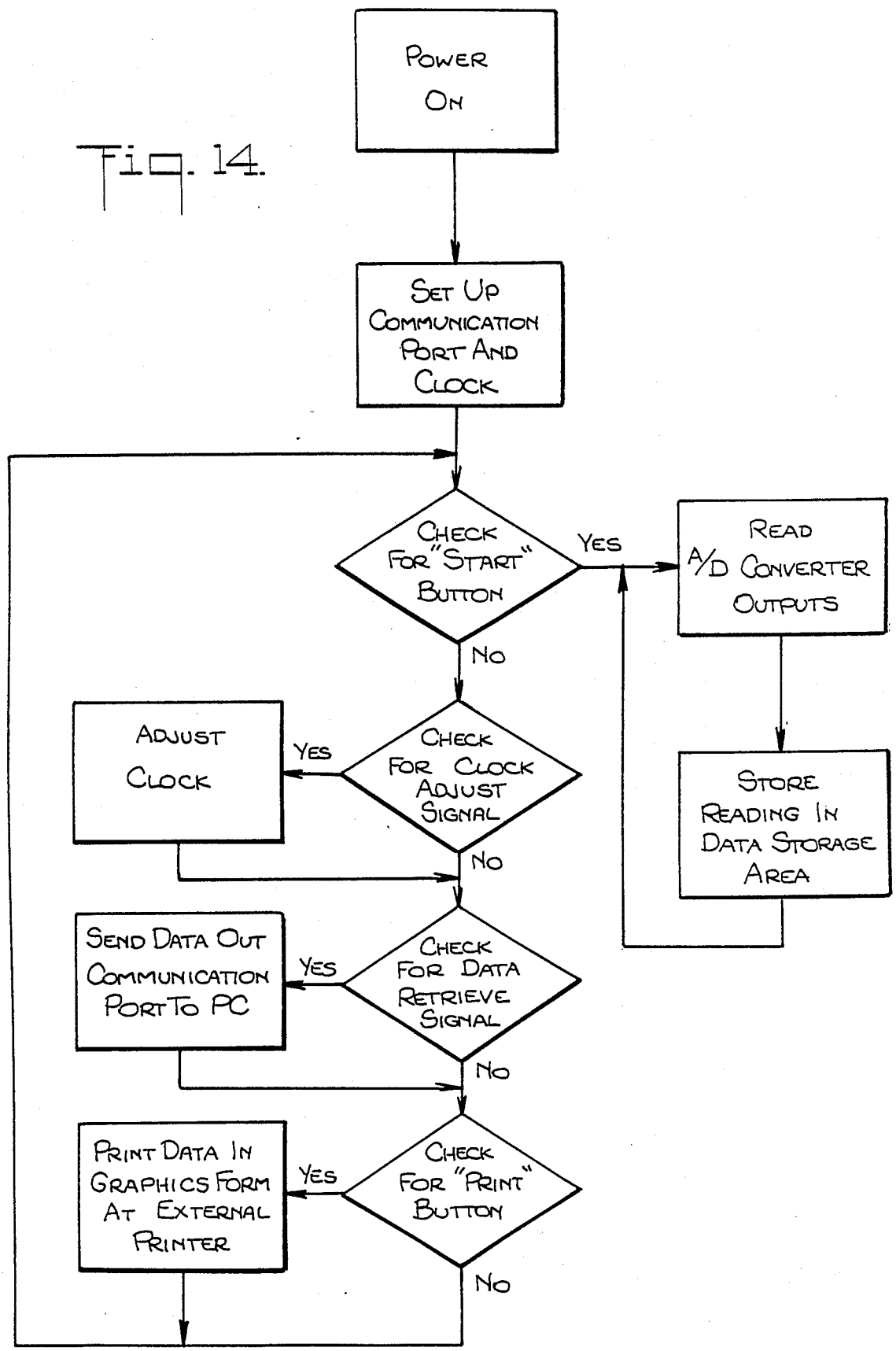
FIG. 14 is a simplified schematic software flow chart for the monitoring device.

Software for controlling the monitor is schematically indicated in FIG. 14. When power is turned on, the software goes through a "housekeeping" routine setting up the communication port 58, the clock 60, the data retrieve signal and a print button (not shown) on the monitor 42. The "housekeeping" routine determines whether a start button (not shown) in the monitor 42 has been depressed and checks whether there is a need to adjust the clock setting such as the time and date.

The "housekeeping" functions also check whether there is a request from the personal computer (not shown) to dump the data or retrieve the data.

In addition, the housekeeping function checks whether the print button (not shown) on the monitor 42 has been pushed to enable the monitor to control the printing of a graph.

Once power has been turned on, the housekeeping functions are continuously checked until the start button (not shown) on the monitor 42 is depressed. When the start button is depressed, the microcomputer 54 records the date and time in the data storage unit 56 and the housekeeping function checks that all systems are in operation.

At the start of the monitoring operation a calibration is performed wherein the microcomputer 54 reads the sensor signal for the flaccid condition of the penis and establishes a base line for the patient being monitored. The microcomputer can be programmed to record the output of the sensors during preselected time intervals such as every 30 seconds for example. Data is thus transmitted from the sensors 10 to the analog-to-digital converter 52 and stored in the data storage unit 56 as previously described.

The monitor 42 using batteries of the type described, is capable of recording up to three nights of nocturnal penile activity, recording changes transmitted by the sensor devices 10 and converting such data to a format which can be outputted to a printer/ recorder (not shown) or to a remote personal computer (not shown).

The recording session ends when the monitor 42 is turned off. The monitor 42 retains the recorded data until it is reset by a clinician. The clinician can connect the monitor 42 to a remote recorder/printer (not shown) and then can press a print button (not shown) on the monitor to enable the recorder/printer to start printing the stored tumescence and rigidity data from the data storage unit 56.

When testing is completed the sensor device 10 can be detached from the ambulatory monitor 42 and disposed of.

The precise dimensions of the sensor device 10 may vary. Nevertheless, to exemplify the magnitudes being dealt with, the foldable member can have a length of approximately 7 to 15 cm. and a width of approximately 1.5 to 2 cm. The layers of foam material 22 and 24 can be approximately 0.5 to 1.5 cm. thick with the foam material 24 being approximately 0.5 to 0.75 cm. in diameter.

The force-sensing resistor 26 can have a printed sheet size of approximately 1 cm. by 1.1 cm. and the force-sensing resistor 28 can have a printed sheet size of approximately the same diameter as the relatively rigid foam material 24.

Another embodiment of the tumescence and rigidity sensor is generally indicated by the reference number 70 in FIG. 16. The sensor device 70 includes a flexible, foldable member 72 of substantially the same construction as the foldable member 12. One end portion of the foldable member 72 includes a securement portion 74, having Velcro hooks 76 provided thereon. An opposite end portion of the foldable member includes Velcro mesh 78, to hold the foldable member 74 in a looped configuration as shown, for example, in FIG. 16.

Relatively soft compressible, conductive foam material 80 is joined to the flexible, foldable, foldable member 72 occupying part of the width of the foldable member 72 and extending to the securement portion 74. An equivalent length of relatively harder compressible, conductive foam material 82 fills out the remaining width of the foldable member 72.

The relatively soft conductive foam material 80 includes spaced crest portions 84 and 86 that extend longitudinally of the foldable member 72. The relatively hard conductive foam material 82 includes a spaced crest portion 88 also extending longitudinally of the foldable member 72.

The conductive foam materials 80 and 82 can be formed in the manner shown and suggested in the article entitled "Robotic Tactile Sensing" by Kirk E. Pennywit in the January 1986 edition of Byte. The conductive foams 80 and 82 can be conductive elastomers, that are elastic, rubber-like materials having electrically conductive properties.

The aforementioned article on Robotic Tactile Sensing indicates that many different conductive elastomers or conductive foam materials have been experimented with, but most designs use an approach wherein a flat hard conductor is pressed against another that is rounded and compressible. The area of the electrical contact will vary according to how hard the first conductor is pushed. The greater the pressure, the larger the contact area formed and the lower the electrical resistance.

The foregoing article also describes the use of sheets of a material known as anisotropically conductive silicone rubber. Anisotropically conductive silicone rubber has the property of being conductive along only one axis in the plane of the sheet.

Other articles relating to conductive silicone rubbers are cited in the foregoing article including the following: "A Force Transducer Employing Conductive Silicone Rubber" by John A. Pubrick in First Robot Vision and Sensors Conference in 1981.

Referring to FIG. 17, a noncompressible conductive flexible strip 90 is disposed on the crest portions 84, 86 and 88 of the conductive foam materials 80 and 82 and need not be bonded to the foam materials 80 and 82. The conductive strip 90 which extends the length and width of the foam materials 80 and 82 can be formed of graphite welded silicone or silver welded silicone, for example, and can have a thickness of approximately 0.1 to 0.2 cm.

Referring to FIG. 16, the sensor device 70 also includes a cable 92 having conductors extending from the respective foam materials 80 and 82 and a cable 94 having a conductor extending from the conductive strip 84 such as with conductive adhesive joined in any suitable known manner.

In using the sensor device 70, the foldable member 72 is formed into a loop around a flaccid penis 13 in a manner similar to that previously described for the sensor 10. The sensor device 70 can be trimmed to size, with scissors, for example, to conform exactly to the contour of the penis 13 in the flaccid condition. Sensor devices 70 can be provided at the base and tip end of the penis 13 as shown in FIG. 16. The sensor devices 70 are detachably connected to an ambulatory monitor 96 that is functionally similar to the ambulatory monitor 42.

During monitoring, the surface contact between the crest portions 84, 86, and 88 and the conductive strip 90 will vary in accordance with the changes in tumescence and rigidity of the penis 13. A base line calibration is made by the monitor 96 at the start of the monitoring operation from the initial conductivity characteristics of the foams 80 and 82 when the penis 13 is in the flaccid condition.

Should tumescence develop, the flat, noncompressible conductor 90, under the influence of penile expansion, presses against the crests 84 and 86 of the relatively soft, compressible conductive foam material 80 in the manner shown in FIG. 21. The contact area between the crests 84, 86 and the conductive strip 90 will thus increase as tumescence increases. Increases or decreases in conductivity between the conductive strip 90 and the crests 84 and 86 are detected, recorded and converted to any selected format by the ambulatory monitor 96.

If a tumescent condition is not accompanied by penile rigidity, the crests 84 and 86 will compress to a greater extent than the crest 88 which will have no significant compression.

During a tumescent condition with accompanying rigidity, penile pressure on the conductive strip 90 will cause compression of the crest 88. The increase in conductive area between the conductive strip 90 and the respective crest portions 84, 86 and 88 will furnish a signal that correlates with the amount of rigidity and tumescence. Electric signals from the sensor device 70 will thus correspond in magnitude to the contact area between the conductive strip 84 and the foam material 80 and 82 to provide a measure of tumescence and rigidity of the penis 13.

Strip charts and other recordings of the tumescence and rigidity signals are obtainable in a manner similar to that previously described for the sensor device 10.

Another embodiment of the tumescence and rigidity sensor is generally indicated by the reference number 100 in FIG. 22. The sensor device 100 differs from the sensor device 70 by provision of relatively soft compressible conductive foam material 102 that occupies part of the width of an foldable member 104.

The conductive foam material 102 includes a plurality of corrugations or crests 106 that extend in a transverse direction relative to the foldable member 104. A relatively hard conductive foam material 108 (FIG. 24) includes a plurality of crests or corrugations 110 that align with the crests 106 to fill out the width of the foldable member 104. A conductive strip 112 identical to the conductive strip 90 is disposed on the crest portions 106 and 110.

The crests 104 of the relatively soft conductive foam material 102 compress and increase in contact area with the conductive strip 112 in response to increases of penile tumescence. The crests 110 of the relatively hard conductive foam material 108 will compress and increase in contact area with the conductive strip 112 only in response to the development of penile rigidity.

Operation of the sensor device 100 is otherwise similar to the operation of the sensor device 70.

Further embodiments of the invention include the conductive foam embodiments shown in FIGS. 25-27. The 25 flexible, foldable member and conductive strip which are combined with the embodiments of FIGS.

25-27 are identical to the foldable members and conductive strips of the sensor devices 70 and 100 and are omitted from FIGS. 25-27 for purposes of facility of description.

The conductive foam embodiment of FIG. 25 includes a relatively soft foam material 120 having rows of spaced crests 122 that are transversely and longitudinally spaced. A relatively hard conductive foam material 124 is disposed alongside the soft foam material 120 with spaced crests 126 that are similarly shaped to the crests 122. The crests 122 and 126 contact a conductive strip (not shown) similar to the conductive strip 84 to provide differences in surface contact that are correlatable with electrical signals of corresponding magnitude to provide data that is indicative of penile tumescence and rigidity.

The conductive foam embodiment of FIG. 26 includes a section of relatively soft conductive foam material 130 having a plurality of peaked conductive portions 132. A relatively hard conductive foam material 134 is arranged alongside the soft conductive material 130 and includes conductive peaks 136 similar in shape to the peaks 132. Contact between the conductive peaks 132, 136 and a conductive strip similar to the conductive strip 84 provide the variations in contact area which are the basis of distinctive signals indicating changes in penile tumescence and rigidity during nocturnal monitoring.

In the embodiment of FIG. 27, a relatively soft conductive foam material 140 contains crests 142 of pyramid shape. A relatively hard conductive foam material 144 arranged alongside the soft foam material 140 includes pyramid-shaped crests 146. Differences in surface contact between a conductive strip similar to the strip 84 and the crests 142,146 will arise based on changes in penile tumescence and rigidity to provide the sensory signals which are the basis of the monitoring procedure.

It will be apparent that numerous other designs for the soft conductive foam material and hard conductive foam material are possible. The main criteria for such design is that the surface contact between such conductive foam materials and the conductive strip vary in response to changes in penile tumescence and rigidity to provide changes in electrical signals that indicate the physiological changes in the penis that take place during monitoring.

Some advantages of the present invention evident from the foregoing description include a nocturnal penile tumescence and rigidity sensor that is easily installed on a patient and easily adapted for exact conformity with the penile contour of a patient. The sensor device is simple to install and, when properly sized, can be installed by the patient just prior to the monitoring session. The sensor devices are easily connected to or disconnected from a monitor, and can be disposed of after testing is completed.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A nocturnal penile tumescence and rigidity sensor comprising:
    a. a flexible, foldable member,
    b. means for securing said foldable member around the penis in the form of a loop,
    c. tumescence sensing means joined to said foldable member for sensing penile tumescence, said tumescence sensing means including foam material joined to said foldable member, said foam material projecting from said foldable member toward said penis when said foldable member is formed into said loop such that said foam material receives compressive forces due to penile tumescence under preselected conditions of penile tumescence, said tumescence sensing means including means responsive to compression of said foam material for providing an electrical output signal proportional to the amount of said compressive force imposed by said penis on said foam material under said condition of penile tumescence when said foldable member is formed into said loop, and
    d. rigidity sensing means joined to said foldable member for sensing penile rigidity.

2. A nocturnal penile tumescence and rigidity sensor comprising:
    a. a flexible foldable member,
    b. means for securing said foldable member around the penis in the form of a loop,
    c. tumescence sensing means joined to said foldable member for sensing penile tumescence, and
    d. rigidity sensing means joined to said foldable member for sensing penile rigidity, said rigidity sensing means including a foam material joined to said foldable member, said foam material projecting from said foldable member toward said penis when said foldable member is formed into said loop such that said foam material receives compressive forces due to penile rigidity under preselected conditions of penile rigidity, said rigidity sensing means including means responsive to penile rigidity forces imposed on said foam material for providing an electrical output signal proportional to the amount of said compressive force imposed by said penis on said foam material under said conditions of penile rigidity when said foldable member is formed into said loop.

3. A nocturnal penile tumescence and rigidity sensor comprising
    a. a flexible foldable member disposable around a penis,
    b. first and second foam materials having different compressibilities joined to said foldable member,
    c. means associated with said first foam material for providing a first electrical signal output corresponding to penile tumescence,
    d. means associated with said second foam material for providing a second electrical signal output corresponding to penile rigidity.

4. The nocturnal penile tumescence and rigidity sensor as claimed in claim 3 wherein said means for providing said first electrical output signal is provided between said first foam material and said elongated member.

5. The nocturnal penile tumescence and rigidity sensor as claimed in claim 4 wherein said means for providing said first electrical output signal includes a force-sensing resistor.

6. The nocturnal penile tumescence and rigidity sensor as claimed in claim 3 wherein said means for providing said first electrical output signal include electrically conductive means within said first foam material.

7. The nocturnal penile tumescence and rigidity sensor as claimed in claim 3 wherein said means for providing said second electrical output signal is provided between said second foam material and said foldable member.

8. The nocturnal penile tumescence and rigidity sensor as claimed in claim 7 wherein said means for providing said second electrical output signal includes a force-sensing resistor.

9. The nocturnal penile tumescence and rigidity sensor as claimed in claim 3 wherein said means for providing said second electrical output signal include electrically conductive means within said second foam material.

10. The nocturnal penile tumescence and rigidity sensor as claimed in claim 3 wherein said foldable member has a predetermined surface area, said first foam material being joined to a major surface area of said foldable member and said second foam material being joined to a minor surface area of said foldable member.

11. The nocturnal penile tumescence and rigidity sensor as claimed in claim 3 wherein said first foam material is electrically conductive.

12. The nocturnal penile tumescence and rigidity sensor as claimed in claim 3 wherein said second foam material is electrically conductive.

13. The nocturnal penile tumescence and rigidity sensor as claimed in claim 3 wherein said first and second foam materials are electrically conductive.

14. The nocturnal penile tumescence and rigidity sensor as claimed in claim 13 further including a conductive flexible elongated member in surface contact with said first and second foam materials to permit electricity to flow through said first and second foam materials and said conductive member.

15. The nocturnal penile tumescence and rigidity sensor as claimed in claim 14 wherein said foldable member and said conductive foldable member are spaced from each other.

16. The nocturnal penile tumescence and rigidity sensor as claimed in claim 15 wherein said first and second foam materials are disposed between said foldable member and said conductive foldable member.

17. The nocturnal penile tumescence and rigidity sensor as claimed in claim 14 wherein said first and second foam materials have respective predetermined shapes in cross-section to provide respective initial preselected surface contact between said first and second foam materials and said conductive member when said penis is in a flaccid condition, the amount of surface contact between said first and second foam materials and said conductive member increasing respective preselected amounts from said respective initial preselected amounts from said respective preselected conductivities through said first and second foam materials in said conductive member in response to predetermined increases in penile tumescence and rigidity, whereby said first and second foam materials and said conductive member comprise said means for providing said first and second electrical output signals corresponding to penile tumescence and rigidity.

18. The nocturnal penile tumescence and rigidity sensor as claimed in claim 3 including means for detachably securing said foldable member around the penis in the form of a loop.

19. The nocturnal penile tumescence and rigidity sensor as claimed in claim 18 wherein said securing means are operable to provide a loop of selectable circumference.

20. The nocturnal penile tumescence and rigidity sensor as claimed in claim 3 wherein said first and second foam materials are joined to said foldable member and project from said foldable member toward said penis when said foldable member is disposed around said penis.

21. The nocturnal penile tumescence and rigidity sensor as claimed in claim 20 wherein said second foam material extends along substantially the entire circumference of said loop.

22. The nocturnal penile tumescence and rigidity sensor as claimed in claim 3 wherein said first foam material has a predetermined compressibility that, under predetermined conditions of penile tumescence, enables said first electrical output signal to be proportional to the amount of force on said first foam material under said condition of penile tumescence when said foldable member is disposed around said penis in the form of a loop.

23. The nocturnal penile tumescence and rigidity sensor as claimed in claim 3 wherein said second foam material has a predetermined compressibility that, under predetermined conditions of penile rigidity, enable said second electrical output signal to be proportional to the amount of force on said second foam material under said conditions of penile rigidity when said foldable member is disposed around said penis in the form of a loop.

24. The nocturnal penile tumescence and rigidity sensor as claimed in claim 3 wherein said first foam material is more compressible under a preselected force than said second foam material.

25. A nocturnal penile tumescence and rigidity sensor comprising:
  a. a flexible, foldable member,
  b. means for securing said foldable member around the penis in the form of a loop,
  c. tumescence sensing means joined to said foldable member for sensing penile tumescence, said tumescence sensing means including a first deformable foam material projecting from said foldable member toward said penis when said foldable member is formed into said loop, said first deformable foam material having a first preselected compressibility to permit compression under predetermined conditions of penile tumescence when said foldable member is formed into said loop around said penis, said tumescence sensing means including means responsive to compression of said first deformable foam material for providing a first electrical output signal proportional to the amount of compressive force imposed by said penis on said first deformable foam material under said condition of penile tumescence when said foldable member is formed into said loop, and
  d. rigidity sensing means joined to said foldable member for sensing penile rigidity, said rigidity sensing means including a second foam material projecting from said foldable member toward said penis when said foldable member is formed into said loop, said second foam material having a second preselected compressibility different from said first preselected compressibility such that said second foam material is less compressible under a preselected force than said first foam material, said rigidity sensing means including means responsive to penile rigidity forces imposed on said second foam material for providing a second electrical output signal proportional to the amount of force imposed by said penis on said second foam material under said conditions of penile rigidity when said foldable member is formed into said loop.

26. A method of measuring penile tumescence and rigidity comprising:
   a. securing first and second foam materials having different compressibility to a flexible foldable member with corresponding first and second signal producing agents and wrapping the foldable member around a penis to permit the expansive pressure of penile tumescence and penile rigidity to produce respective tumescence and rigidity forces on the respective first and second foam materials,
   b. producing a first electrical signal from the first signal producing agent when the first foam material compresses under force conditions caused by penile tumescence,
   c. producing a second electrical signal from the second signal producing agent when the second foam material responds to force conditions caused by penile rigidity,
   d. sensing the first electrical signal from the first signal producing agent in response to the penile tumescence force imposed on the first foam material and interpreting the first electrical signal to measure tumescence, and
   e. sensing the second electrical signal from the second signal producing agent in response to the penile rigidity force imposed on the second foam material and interpreting the second electrical signal to measure rigidity.

27. The method of claim 26 including continuously recording the measurements of penile tumescence and rigidity over a preselected period of time to provide a continuous readout of tumescence and rigidity characteristics during said preselected time period.

* * * * *

UNITED STATES PATENT AND TRADEMARK OFFICE
CERTIFICATE OF CORRECTION

PATENT NO. : 4,913,162
DATED : April 3, 1990
INVENTOR(S) : William N. Leang, et al.

It is certified that error appears in the above-identified patent and that said Letters Patent is hereby corrected as shown below:

In the Title, change "TUMESCENE" to --TUMESCENCE--.

In the Abstract, line 1, change "TUMESCENE" to --TUMESCENCE--.

At column 1, at the title, change "TUMESCENE" to --TUMESCENCE--.

At column 2, line 5, change "patent" to --patient--.

At column 6, line 7, change "flexible" to --foldable--.

At column 9, line 9, delete "foldable" (second occurrence).

At column 10, line 66, delete "25".

At column 13, line 58, after "preselected" insert --surface contact to provide--.

At column 13, line 59, delete "amounts from said".

Signed and Sealed this

Eighteenth Day of June, 1991

*Attest:*

HARRY F. MANBECK, JR.

*Attesting Officer*  *Commissioner of Patents and Trademarks*